Figure 1:
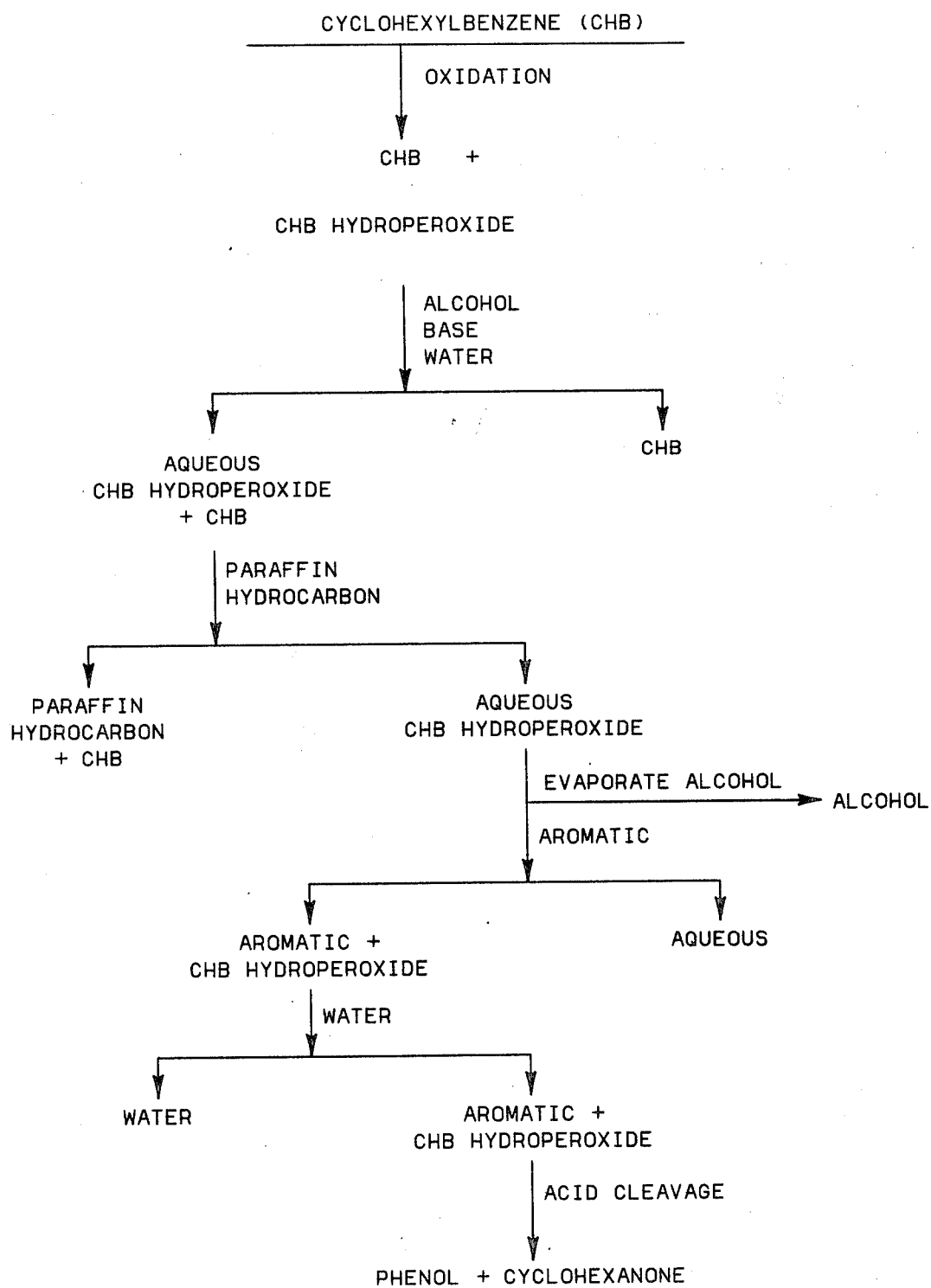

United States Patent [19]

Wu

[11] 4,120,902

[45] Oct. 17, 1978

[54] OXIDATION PRODUCT RECOVERY

[75] Inventor: Yulin Wu, Bartlesville, Okla.

[73] Assignee: Phillips Petroleum Company, Bartlesville, Okla.

[21] Appl. No.: 775,144

[22] Filed: Mar. 7, 1977

[51] Int. Cl.$^2$ .................. C07C 27/04; C07C 27/34; C07C 37/08; C07C 45/24

[52] U.S. Cl. .................. 260/586 R; 260/465 F; 260/586 P; 260/593 A; 260/592; 260/610 A; 260/613 R; 260/613 D; 260/674 SE; 568/798; 568/754; 568/774; 568/741; 568/780; 568/781; 568/706; 568/708; 568/736

[58] Field of Search .......... 260/586 P, 586 R, 610 A, 260/610 B, 621 C, 593 A, 619 R, 619 A, 619 D, 465 F, 626 T, 619 F, 622 R, 622 P, 613 R, 613 D, 623 R, 624 R, 592, 620

[56] References Cited

U.S. PATENT DOCUMENTS

| | | | |
|---|---|---|---|
| 2,430,864 | 11/1947 | Farkas et al. | 260/610 A |
| 2,915,558 | 12/1959 | Alders et al. | 260/610 A |
| 3,190,923 | 6/1965 | Sodomann et al. | 260/610 A |
| 3,821,314 | 6/1974 | Arkell et al. | 260/610 A |

FOREIGN PATENT DOCUMENTS

| | | | |
|---|---|---|---|
| 2,352,580 | 6/1974 | Fed. Rep. of Germany | 260/610 A |
| 1,151,287 | 5/1969 | United Kingdom | 260/610 A |
| 743,736 | 1/1956 | United Kingdom | 260/610 A |
| 786,340 | 11/1957 | United Kingdom | 260/610 A |
| 920,013 | 3/1963 | United Kingdom | 260/610 A |

*Primary Examiner*—Norman Morgenstern

[57] ABSTRACT

A process for the separation and purification of reaction product from the oxidation of hydrocarbyl aromatic compounds to hydrocarbyl aromatic hydroperoxides is provided comprising (1) extracting the oxidation effluent with an aqueous alcoholic base, (2) contacting the aqueous phase thus produced with a paraffin hydrocarbon solvent to remove residual unoxidized hydrocarbyl aromatic, (3) extracting the aqueous hydrocarbyl aromatic hydroperoxide phase remaining with an aromatic solvent, and (4) washing of the hydroperoxide-containing aromatic phase with water to remove base. The resulting hydroperoxide phase substantially free of unoxidized hydrocarbyl aromatic can be subjected to acid-catalyzed cleavage to produce hydroxy aromatic and carbonyl compound products without encountering the problem of azeotrope formation between unoxidized hydrocarbyl aromatic reactant with cleavage product.

8 Claims, 2 Drawing Figures

*FIGURE 2*

OXIDATION PRODUCT RECOVERY

This invention relates to a process for the separation and purification of oxidation reaction products. In accordance with another aspect, this invention relates to the purification and separation of oxidation products by multiple extraction employing different solvents to obtain hydroperoxide essentially free of unoxidized aromatic reactants that can be acid-catalyzed to form cleavage products. In a further aspect, this invention relates to the separation of hydroperoxide from oxidation products containing unoxidized aromatic reactants by solvent extraction with a solvent mixture comprising an aqueous alcoholic base followed by extraction with a paraffinic hydrocarbon. In accordance with a further aspect, this invention relates to a process comprising multiple extractions to separate hydrocarbyl aromatic hydroperoxides from other oxidation products, utilizing successively an alcohol-base-water-solvent mixture, a paraffin solvent, and an aromatic solvent. In accordance with a further aspect, this invention relates to a process of removing residual unoxidized hydrocarbyl aromatic reactants from oxidation products containing hydrocarbyl aromatic hydroperoxides by multiple solvent extractions prior to acid cleavage of the hydroperoxide to hydroxy aromatic and carbonyl compound cleavage products to avoid azeotrope formation of unoxidized aromatic reactants with cleavage products.

It is known in the art that hydrocarbyl aromatics, such as cyclohexylbenzene, can be converted to a hydroxy aromatic compound, such as phenol, and a carbonyl compound, such as cyclohexanone, via cycloalkyl aromatic hydroperoxide, e.g., cyclohexylbenzene hydroperoxide. It has been found that the presence of unoxidized cyclohexylbenzene in the cyclohexylbenzene hydroperoxide results in difficulty during purification of the hydroperoxide cleavage products (phenol and cyclohexanone) by distillation with cyclohexylbenzene appearing in the products due to azeotrope formation of cyclohexylbenzene (CHB) with the cleavage products and to the high boiling point of the CHB. The instant invention provides a method of removing residual cyclohexylbenzene from cyclohexylbenzene hydroperoxide before acid cleavage of the hydroperoxide to phenol and cyclohexanone.

Accordingly, an object of this invention is to provide a process for converting hydrocarbyl-substituted aromatic compounds to hydroxy compounds and carbonyl compounds.

A further object of this invention is to provide a process for the purification and separation of hydrocarbyl aromatic oxidation products.

Another object of this invention is to provide a process for the separation and recovery of unoxidized hydrocarbyl aromatics present in hydrocarbyl aromatic oxidation products.

A further object of this invention is to provide a process for the separation of cyclohexylbenzene from cyclohexylbenzene hydroperoxide.

A further object of this invention is to provide a process for the purification of the crude reaction product from the oxidation of cyclohexylbenzene to cyclohexylbenzene hydroperoxide.

Other objects, aspects, and the several advantages of the invention will be apparent to those skilled in the art upon a study of the specification and the appended claims.

In accordance with the invention, a process is provided for the purification and separation of oxidation products following oxidation of hydrocarbyl aromatics to separate unoxidized hydrocarbyl aromatics therefrom comprising multiple solvent extractions with different solvents under conditions which yield a hydrocarbyl aromatic hydroperoxide product essentially free of unoxidized hydrocarbyl aromatic reactants.

In accordance with one embodiment of the invention, the reaction product from the oxidation of a hydrocarbyl aromatic to a hydrocarbyl aromatic hydroperoxide is purified by first extracting with an aqueous alcoholic base followed by extracting with a paraffinic hydrocarbon solvent and then an aromatic hydrocarbon solvent, thereby yielding hydroperoxide essentially free of unoxidized hydrocarbyl aromatic reactant.

In accordance with one preferred embodiment of the invention, purification of the reaction product obtained upon the oxidation of cyclohexylbenzene (CHB) to cyclohexylbenzene hydroperoxide (CHB—OOH) is achieved by (1) extraction with an aqueous alcoholic base, (2) contacting of the aqueous layer with a paraffinic hydrocarbon solvent to remove residual cyclohexylbenzene, (3) optional removal of alcohol, for example, by vaporization, (4) extraction of an aqueous cyclohexylbenzene hydroperoxide phase with an aromatic solvent such as benzene, (5) removal of base from the aromatic phase by washing with water, leaving a cyclohexylbenzene hydroperoxide phase essentially free of cyclohexylbenzene. The resulting aromatic phase containing cyclohexylbenzene hydroperoxide can be subjected to acid-catalyzed cleavage of the hydroperoxide to form hydroxy aromatic compounds and carbonyl compounds.

The instant invention is applicable to the treatment of hydroperoxide-containing oxidation mixtures obtained by the oxidation of hydrocarbyl-substituted aromatic compounds having up to 30 carbon atoms and the general formula

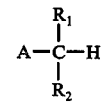

wherein $R_1$ and $R_2$ are either a hydrogen; an alkyl, preferably a lower alkyl; or an aryl group; or wherein $R_1$ and $R_2$ taken together form a cycloalkyl ring having from 4 to 7 carbon atoms; and wherein A is an aryl or substituted aryl group, with the substituent groups being one or more or a mixture of alkyl, alkoxy, halogen, nitro, cyano, cycloalkyl, or the like. The aryl group A may be either mononuclear, i.e., phenyl, or polynuclear, i.e., naphthyl, and the like. Specific examples of suitable compounds to be oxidized for use in the instant invention include toluene, ethylbenzene, isopropylbenzene, secbutylbenzene, p-diisopropylbenzene, p-methoxy isopropylbenzene, p-chloro isopropylbenzene, p-nitro isopropylbenzene, p-cyano isopropylbenzene, cyclohexylbenzene, cyclopentylbenzene, cycloheptylbenzene, diphenyl methane. 1-ethylnaphthalene, 1-isopropylnaphthalene, 1-cyclohexylnaphthalene, 1-(1-naphthyl)octadecane, 1-(2-naphthyl)octadecane, 1-(1-naphthyl)eicosane, 1,4-dicyclohexylbenzene, and the like.

Oxidation of hydrocarbyl aromatic compounds to form hydroperoxides can be carried out under a wide range of temperature conditions and pressure with or without catalyst, etc., as is well known in the art. Compounds represented in the above general formula are generally oxidized within a temperature range of from 25° C. to 250° C. and preferably from 60° C. to 160° C. The oxidation is carried out within a time range of from 5 minutes up to 5 days and preferably from 15 minutes up to 24 hours.

The oxidation reaction can be carried out with the use of essentially pure oxygen or mixture of oxygen with inert gases. Air is generally used as the source of oxygen for the reaction according to this invention. The amount of oxygen employed is not particularly critical and can be in the range of from atmospheric pressure up to 700 psig of oxygen or preferably from 50 up to 350 psig of oxygen. If mixtures of oxygen with other gases are employed, the above figures refer to the partial pressure of oxygen in said mixtures. The oxidation reaction can be carried out simply by passing the oxygen containing gas through the compound being oxidized under the above-described conditions of time, temperature, and oxygen pressure. It is also within the scope of this invention to employ suitable oxidation initiators or catalysts which are known in the art. It is also possible to carry out the oxidation reaction in the presence of suitable amounts of base to neutralize acidic materials which can be formed as by-products in the oxidation reaction. This latter feature is also known in the art. The crude oxidation product is generally filtered to remove insoluble salts which may have formed.

The reaction product of the oxidation of hydrocarbyl aromatic compounds such as cyclohexylbenzene (CHB) to hydroperoxide, e.g., cyclohexylbenzene hydroperoxide, contains unoxidized aromatic reactant, and, in accordance with the invention, the reaction product is subjected to solvent extraction by contacting with an aqueous alcoholic base under extraction conditions which remove hydrocarbyl aromatic hydroperoxide leaving unoxidized hydrocarbyl aromatic which can be recycled to oxidation. The conditions for carrying out the first extraction can vary appreciably, and the conditions employed including temperature and pressure normally are sufficient to effect substantial separation of the hydrocarbyl aromatic hydroperoxide from unoxidized hydrocarbyl aromatic reactant.

The base used in the extraction step can be water-soluble oxides, hydroxides, carbonates, bicarbonates, phosphates, or hydrogen phosphates of sodium, potassium, lithium, calcium, barium, strontium, and magnesium. Ammonia and water-soluble amines such as ethylamine, diethylamine, trimethylamine, and the like can also be used. Sodium hydroxide is the presently preferred base. The amount of base used will be broadly from about 0.05 to about 20, preferably about 0.2 to 5 moles of base per mole of hydroperoxide.

The alcohol used in this extraction step is preferably water soluble and can be a lower monohydroxy alcohol having from one to about six carbon atoms, such as methanol, ethanol, 1-propanol, 2-propanol, 1-butanol, 2-butanol, and the like, a dihydroxy alcohol such as ethylene glycol, 1,2-propanediol, 1,3-propanediol, and the like, or a polyhydroxy alcohol such as glycerol. The amount of alcohol used in the extraction step will be broadly about 0.1 to about 100, preferably about 1 to 50 moles of alcohol per mole of hydroperoxide.

Water is used in the first extraction in an amount broadly ranging from about 0.1 to about 50, preferably about 1 to 10 parts by weight of water per part by weight of base. Temperatures to be used for this extraction will broadly range from 0° C. to 60° C., preferably 10° C. to 40° C.

According to the instant invention, the aqueous hydrocarbyl aromatic hydroperoxide phase, which also contains alcohol and base, is subjected to solvent extraction using a paraffin hydrocarbon including straight chain, branched, and cyclic paraffins, preferably having 3–10 carbons per molecule. Suitable paraffin hydrocarbons that can be used include propane, butanes, pentanes, hexanes, heptanes, octanes, cyclopentane, cyclohexane, and the like, and mixtures thereof. The mixture of alcohol, base, and water, containing hydrocarbyl aromatic hydroperoxide is contacted with a paraffin hydrocarbon under suitable extraction conditions such that the unoxidized hydrocarbyl aromatic reactant remaining in the solvent phase is selectively extracted by the paraffin hydrocarbon solvent. Generally, paraffin hydrocarbons are used in amounts ranging from about 0.005 to about 10, preferably about 0.05 to 3 parts by weight of paraffin hydrocarbon to one part by weight of aqueous phase. The temperature used for said extraction will be generally from about 0° C. to about 60° C., preferably about 10° C. to about 40° C.

The hydrocarbyl aromatic hydroperoxide phase obtained following the paraffin hydrocarbon extraction to remove unoxidized hydrocarbyl aromatic reactant can be passed directly to a subsequent extraction for contacting with an aromatic solvent, as defined hereinbelow, or prior to said extraction be subjected to treatment so as to remove alcohol remaining from the initial solvent mixture.

The aqueous hydroperoxide, which also contains alcohol and base, can be distilled, preferably under reduced pressure, to vaporize the alcohol. This step is not considered an essential step to the instant invention.

According to the instant invention, the aqueous hydrocarbyl aromatic hydroperoxide phase (with alcohol present or with alcohol removed by distillation) is extracted with an aromatic solvent to remove the hydroperoxide from the aqueous phase. Aromatic compounds that can be used for this extraction to remove hydroperoxide from the aqueous phase include monocyclic aromatics including substituted aromatic compounds. Representative aromatic solvents that can be used include benzene, xylenes, toluene, chlorobenzene, anisole, and the like, and mixtures thereof. The amount of aromatic solvent used in this extraction will generally be from about 0.01 to 100, preferably 0.1 to 10 parts by weight of aromatic solvent to one part by weight of aqueous hydroperoxide solution. Temperatures used for this extraction will generally range from about 0° C. to 60° C., preferably 10° C. to 40° C. It should be understood, however, that the extraction conditions can be varied substantially so long as conditions are employed that selectively remove the hydroperoxide from the aqueous phase leaving an aqueous phase containing alcohol and at least a portion of the base.

According to the instant invention, the aromatic extract containing the hydroperoxide is washed with water to remove traces of base (alkali) present in the aromatic solution. The amount of water used will generally range from about 0.005 to about 100, preferably 0.05 to 10 parts by weight to one part by weight of the aromatic solution. The temperature used will range from about 0° C. to 60° C., preferably 10°–40° C. The condition can vary from those set forth above and are sufficient to remove traces of base present in the aromatic solution so as to leave a mixture of aromatic solvent and hydroperoxide which can be further treated as desired.

According to the instant invention, the hydroperoxide formed by oxidation of the above-described suitable compounds is subjected to an acid-catalyzed cleavage in a suitable reaction medium. The aromatic solution of the hydroperoxide can be used directly or the aromatic solvent can be removed by distillation, preferably under reduced pressure, and another reaction medium added to the hydroperoxide.

The method used for the hydroperoxide cleavage is not critical to the instant invention and any method known in the art can be employed. For example, strong protonic acids such as sulfuric acid, arylsulfonic acids, e.g., p-toluenesulfonic acid, trifluoroacetic acid, and the like, can be used for the cleavage of the hydroperoxide.

The hydroperoxide cleavage product can be treated in a manner that is suitable for the method of cleavage used. For example, if a strong protonic acid were used for the hydroperoxide cleavage, there will generally be an aqueous phase and an organic phase at the conclusion of the cleavage reaction. If there is only one phase present, suitable amounts of water can be added to form a separate aqueous phase containing most of the strong acid cleavage catalyst and an organic phase containing essentially all of the cleavage products, which are not appreciably soluble in water. The aqueous phase is separated and the remaining organic phase is neutralized with a suitable amount of base such as an alkali metal hydroxide or carbonate or an alkaline earth metal hydroxide or carbonate. Ammonia and amines can also be used as neutralizing bases for the organic phase. The amount of neutralizing base is not critical and can easily be determined by common analytical methods. Specifically, the amount of neutralizing base employed will at least be that amount to neutralize the acid present in the organic phase. Generally speaking, an excess of that amount required for this neutralization is usually employed for convenience in speeding up the neutralization reaction. Said organic phase which has been treated with base to neutralize the acid present is then generally filtered to remove insoluble salts and the like which may have formed during the neutralization. The filtrate can then be subjected to various known procedures for separating the products of the cleavage reaction. For example, a fractional distillation or an extractive distillation with sulfolane can be employed to separate phenol and cyclohexanone produced by the cleavage of cyclohexylbenzene hydroperoxide under the conditions broadly disclosed above. Other suitable means known in the art can be employed for separating phenol and the carbonyl-containing compound from the above-described mixtures.

A better understanding of the invention will be obtained upon reference to the accompanying drawings in which:

FIG. 1 presents a simple flow diagram showing the basic features of the instant invention, and FIG. 2 illustrates diagrammatically, including more detail with respect to process equipment and flow lines, one embodiment of the invention for the oxidation of cyclohexylbenzene followed by a series of recovery steps and ultimate recovery of high purity hydroperoxide.

Referring specifically to FIG. 2, cyclohexylbenzene feed is passed by way of line 10 along with promoters in line 11 and an oxygen-containing gas such as air in line 12 and introduced into oxidation zone 14 wherein the cyclohexylbenzene feed is subjected to oxidation conditions as set forth herein for the conversion of cyclohexylbenzene or cyclohexylbenzene hydroperoxide. Cyclohexylbenzene recycle is introduced into oxidation zone 14 by way of line 15.

Oxidation reaction effluent is removed from zone 14 by way of line 16, passed through filtration zone 17 for separation of the salts, and the filtered effluent is then passed by way of line 18 to extraction zone 19 wherein the oxidation effluent is subjected to extraction conditions by contacting with an alcohol-base-water solvent mixture introduced by way of line 20 to zone 19. Within zone 19 the solvent mixture extracts the hydroperoxide and some unoxidized cyclohexylbenzene which is removed from zone 19 and passed by line 21 to a subsequent extraction zone 22. Cyclohexylbenzene remaining in zone 19 can be recycled by way of line 23 and line 15 to oxidation zone 14. Also introduced into zone 19 by way of line 24 is recovered water and base subsequently removed as described hereinbelow.

The aqueous phase containing hydroperoxide and some unoxidized cyclohexylbenzene removed from extraction zone 19 is contacted in extraction zone 22 with a suitable paraffin hydrocarbon which removes unoxidized cyclohexylbenzene by way of line 25 which is passed to a distillation zone 26 wherein paraffin hydrocarbon is recovered for recycle to zone 22 by way of line 27. Fresh paraffin hydrocarbon can be introduced by way of line 28. Cyclohexylbenzene separated from the solvent in zone 26 is passed by way of line 29 for recycle to zone 14.

An aqueous phase containing hydroperoxode and solvent (alcohol-base-water) is removed from zone 22 by line 30 and passed to distillation zone 31 wherein the aqueous phase is subjected to distillation conditions sufficient to remove alcohol remaining from the solvent mixture overhead by way of line 32 which can be recycled to extraction zone 19. The aqueous phase containing hydroperoxide, base, and trace amounts of alcohol is removed from zone 31 by way of line 33 and passed to extraction zone 34 wherein the mixture is contacted under suitable extraction conditions with an aromatic solvent introduced by way of line 35. The aromatic solvent selectively removes the hydroperoxide which mixture is passed by way of line 36 to water wash zone 37. The aqueous phase remaining in zone 34 which contains some base is removed by way of line 38 and recycled to extraction zone 19.

The aromatic phase containing hydroperoxide and some base remaining from the initial extraction zone solvent is subjected to a water wash in zone 37 which water is introduced by way of line 39. Zone 37 is operated under conditions such that an aqueous phase is formed containing base leaving an aromatic phase containing cyclohexylbenzene hydroperoxide which is removed by way of line 40 and can be passed to further treatment as desired, for example, an acid-catalyzed cleavage step to form hydroxy aromatic compound and carbonyl compound cleavage products. The aqueous phase containing base is removed from zone 37 by way of line 41 and can be subjected to distillation to recover water for recycle to zone 37 by way of line 42 with the remainder being passed by way of line 43 for recycle to initial extraction zone 19.

EXAMPLES

The following examples are presented to demonstrate operability for the instant invention. These abbreviations are used in the examples:

CHB = cyclohexylbenzene, and
CHB hydroperoxide = cyclohexylbenzene hydroperoxide.

The amounts of CHB and CHB hydroperoxide present at various points in the separation scheme are presented as a weight percent of the original amount of that material in the starting mixture of CHB and CHB hydroperoxide. Analyses of CHB hydroperoxide were done by iodometric titrations and CHB analyses were done by gas chromatography using butylbenzene as an internal standard.

EXAMPLE I

Run 1 was conducted according to the instant invention in which a 40 g solution containing 6.16 g (32 mmoles) CHB hydroperoxide and 33 g (206 mmoles) of CHB was employed. This solution was stirred for 15 minutes with 12 g (375 mmoles) methanol, 3.2 g (80 mmoles) sodium hydroxide, and 5.86 g water. The CHB layer was separated from the aqueous layer, and the aqueous layer (26.2 g) was washed twice with 5 ml (3.1 g) portions of pentane [total pentane solution = 10 ml (6.2 g)]. The combined pentane extracts contained 1.06 g (3.2 weight percent) CHB. Distillation of the aqueous layer under reduced pressure removed 9.4 g of the methanol. The remaining aqueous phase (15.5 g) was extracted with 10 g benzene, and the benzene layer (17.1 g) was washed once with 1.5 g water. The benzene solution contained 4.3 g (69.8 weight percent) CHB hydroperoxide and 0.08 g (0.24 weight percent) CHB. 29.9 weight percent CHB hydroperoxide was present in the recycle stream.

Another run was made which was similar to the process of the instant invention except that no pentane extraction was done. In Run 2, a 50 g solution containing 7.82 g (40 mmoles) CHB hydroperoxide and 39.65 g (248 mmoles) CHB was employed. This solution was stirred for 15 minutes with 15 g (469 mmoles) methanol, 3.25 g (81 mmoles) sodium hydroxide, and 6.51 g water. The CHB and aqueous layers were separated, and the aqueous layer was distilled under reduced pressure to remove 12.88 g of methanol. 3.23 g of water was added to the remaining aqueous layer, and the total aqueous phase (21.6 g) was extracted twice with 10 g portions of benzene. The combined benzene extracts were washed with 2 g water, and the water wash was extracted with 5 g of benzene. Analysis of the total benzene solution formed by combination of the above benzene extracts showed the presence of 3.50 g (44.8 weight percent) CHB hydroperoxide. Although no CHB analysis was done on the benzene solution, an analysis of the aqueous layer before methanol distillation showed the presence of 1.61 g (4.1 weight percent) CHB. Due to the known benzene solubility of CHB, it is believed that essentially all of this CHB will be present in the benzene solution. The results of Runs 1 and 2 are summarized in Table I.

The results of these two runs show that the separation process of the instant invention (Run 1), which includes a pentane extraction step, results in the separation of CHB hydroperoxide with a very low level of CHB from the oxidation product mixture. A similar separating process without the pentane extraction step (Run 2) does not remove the residual CHB and results in CHB hydroperoxide containing CHB.

TABLE I

| | Run No.: | |
|---|---|---|
| | 1[d] | 2[e] |
| Oxidation Product[a], grams | 40 | 50 |
| Extraction Solution[b], wt. % | | |
| Sodium hydroxide | 8.0 | 6.5 |
| Water | 14.7 | 13.0 |
| Methanol | 30 | 30 |
| CHB Content[c], wt. %: | | |
| Before pentane extraction | 3.5 | 4.1 |
| After pentane extraction | 0.24 | — |
| CHB Hydroperoxide Content, wt. %: | | |
| In aqueous layer[f] | 82.8 | 70.2 |
| In benzene | 69.8 | 44.8 |

[a] Total weight of starting solution containing CHB and CHB hydroperoxide.
[b] Solution added to the oxidation product in the first extraction step. Values listed are weight percent of oxidation product.
[c] CHB content of an aqueous layer before pentane extraction or after pentane extraction.
[d] The separation procedure included a pentane extraction of the aqueous-hydroperoxide layer.
[e] The separation procedure did not include a pentane extraction step.
[f] After or without pentane extraction.

In a separate experiment, 333 g of a solution containing 19.5 weight percent phenol, 19.5 weight percent cyclohexanone, and 61 weight percent CHB was fractionally distilled. The results are shown in Table II. CHB is present in all fractions except for the first few which are pure cyclohexanone. Therefore, attempts to separate by fractional distillation the product mixture obtained from the cleavage of CHB hydroperoxide when CHB is present result in the presence of CHB in most of the fractions.

TABLE II

| Fractions | Weight, grams | Weight as % of Starting Solution[a] | Fraction Composition, Wt. % | | |
|---|---|---|---|---|---|
| | | | Cyclohexanone | CHB | Phenol |
| 1 to 5 | 32.9 | 9.9 | 100 | — | — |
| 6 | 4.1 | 1.2 | 93.3 | 1.7 | 4.6 |
| 7 | 9.0 | 2.7 | 40.3 | 2.9 | 56.6 |
| 8 to 13 | 78.5 | 23.6 | 26.6 to 23 | 1.9 to 2.3 | 71.5 to 74.8 |
| 14 | 7.7 | 2.3 | 19.0 | 13.4 | 67.6 |
| 15 | 10.8 | 3.2 | 0.5 | 97.8 | 1.7 |
| 16 to 19 | 183.6 | 55.1 | trace | 99 | trace |
| Pot Residue | 5.2 | 1.6 | — | — | trace |

[a] Starting solution = 333 g.

EXAMPLE II

Run 3 was made to show the effect of the pentane extraction step on CHB content of the aqueous layer that is separated from the CHB layer. A 10 g solution containing 1.67 g (8.7 mmoles) CHB hydroperoxide and 7.6 g (47.4 mmoles) CHB was stirred with 1.05 g (26.2 mmoles) sodium hydroxide, 3.0 g (93.8 mmoles) methanol, and 1.05 g water. The CHB layer was separated, and the aqueous layer was found to contain 1.62 g (97 weight percent of the original amount) CHB hydroperoxide and 0.5 g (6.6 weight percent of the original amount) CHB. The aqueous layer (5.95 g) was extracted with 1.0 g pentane, and the remaining aqueous layer contained 0.023 g (0.3 weight percent of the original quantity) CHB. Therefore, the pentane extraction lowers the CHB content of the aqueous layer from 6.6 to 0.3 weight percent of the original CHB in the starting solution.

EXAMPLE III

A control run was made to show the importance of base in the first extraction step of the separation sequence. A 5.0 g solution containing 2.8 g CHB and 1.6 g (8.3 mmoles) CHB hydroperoxide was mixed with 5.0 g (156 mmoles) methanol and 1.0 g water. The two layers were separated, and the CHB layer was washed once with a mixture of 0.6 g water and 3.0 g (94 mmoles) methanol. The original aqueous layer and the water-methanol wash were combined and extracted three times with 5 ml portions of pentane. The aqueous layer contained 1.122 g (70 weight percent of the starting quantity) CHB hydroperoxide and 0.114 g (4.1 weight percent of the starting quantity) CHB. The CHB content at the same point in the separation sequence of Run 3 (Example II) where sodium hydroxide was present was 0.3 weight percent of the starting quantity. Therefore, the presence of base is shown to be important to the efficient removal of CHB during the separation.

EXAMPLE IV

A control run was made to show the effect of having only methanol (no water or base) present in the first separation step with the crude oxidation mixture. A 10.0 g solution containing 1.4 g (7.3 mmoles) CHB hydroperoxide and 8.3 g CHB was mixed with 3.0 g (93.8 mmoles) methanol. No separation of phases occurred. Therefore, methanol without base and water is not operable in the practice of the instant invention.

I claim:

1. In a process for the oxidation of hydrocarbyl aromatic compounds with an oxygen-containing gas under conditions which produce hydrocarbyl aromatic hydroperoxides, the steps of separating and recovering oxidation products from the oxidation reaction effluent which comprises:
   (a) contacting the oxidation reaction effluent comprising hydrocarbyl aromatic hydroperoxide and unoxidized hydrocarbyl aromatic reactants with an alcohol-base-water solvent mixture under extraction conditions which form a first aqueous hydrocarbyl aromatic hydroperoxide phase also containing alcohol and base and residual amounts of unoxidized hydrocarbyl aromatic and a hydrocarbyl aromatic phase and separating said first aqueous phase from said aromatic phase;
   (b) extracting said residual amounts of unoxidized hydrocarbyl aromatic solvent under extraction conditions such that said paraffin hydrocarbon extracts said residual unoxidized hydrocarbyl aromatic leaving a second aqueous phase comprising hydrocarbyl aromatic hydroperoxide base and alcohol;
   (c) subjecting said second aqueous phase remaining in (b) to solvent extraction by contacting with an aromatic solvent under extraction conditions which form an extract phase containing aromatic solvent, hydrocarbyl aromatic hydroperoxide, and residual amounts of base and a third aqueous phase and separating said extract phase from said third aqueous phase; and
   (d) washing said extract phase with water to remove residual amounts of base leaving a purified phase of aromatic solvent and hydrocarbyl aromatic hydroperoxide.

2. A process according to claim 1 which comprises the additional steps of
   (e) subjecting the purified phase of (d) to an acid catalyzed cleavage to form hydroxy aromatic compound and carbonyl compound cleavage products and
   (f) recovering cleavage products.

3. A process according to claim 1 wherein at least a portion of the alcohol remaining in said second aqueous phase of (b) is removed therefrom prior to solvent extraction in (c).

4. A process according to claim 1 wherein the solvent in (a) is a mixture of:
   (1) about 0.05 to about 20 moles of base per mole of hydroperoxide;
   (2) from about 0.1 to about 100 moles of alcohol per mole of hydroperoxide; and
   (3) from about 0.1 to about 50 parts by weight of water per one part by weight of base; and the solvent in (b) is a paraffin hydrocarbon having from 3 to 10 carbon atoms.

5. A process according to claim 1 for the oxidation of cyclohexylbenzene to cyclohexylbenzene hydroperoxide which comprises the steps of:
   (a) contacting the oxidation reaction effluent comprising cyclohexylbenzene hydroperoxide and cyclohexylbenzene with an alcohol-base-water solvent mixture in which there is present from about 0.05 to 20 moles of base per mole of hydroperoxide, from about 0.1 to about 100 moles of alcohol per mole of hydroperoxide, and from about 0.1 to about 50 parts by weight of water per weight part of base under extraction conditions to form a first aqueous cyclohexylbenzene hydroperoxide phase also containing alcohol and base and residual amounts of cyclohexylbenzene and a cyclohexylbenzene phase and separating said first aqueous phase from said cyclohexylbenzene phase;
   (b) extracting said residual amounts of cyclohexylbenzene from said first aqueous phase by contacting same with a paraffin hydrocarbon having from 3 to 10 carbon atoms under extraction conditions such that said paraffin hydrocarbon extracts said residual cyclohexylbenzene from said first aqueous phase leaving a second aqueous phase of cyclohexylbenzene hydroperoxide base and alcohol;
   (c) subjecting said second aqueous phase of (b) to conditions of temperature and pressure sufficient to vaporize and remove a substantial portion of the alcohol present in said second aqueous phase leaving a third aqueous phase of cyclohexylbenzene hydroperoxide and base;
   (d) subjecting said third aqueous phase remaining in (c) to solvent extraction by contacting with an aromatic solvent under extraction conditions which form an extract phase containing aromatic solvent, cyclohexylbenzene hydroperoxide, and residual amounts of base and a fourth aqueous phase and separating said extract phase from said fourth aqueous phase; and
   (e) contacting said extract phase with sufficient water to substantially remove residual amounts of base in the aqueous phase thus formed leaving aromatic solvent and cyclohexylbenzene hydroperoxide.

6. A process according to claim 5 comprising the additional steps of:
   (f) subjecting the water-washed phase of (e) substantially freed of base to an acid-catalyzed cleavage to form hydroxy aromatic compound and carbonyl compound cleavage products; and (g) recovering cleavage products.

7. A process according to claim 5 wherein the solvent in (a) is a mixture of methanol, sodium hydroxide, and water, the solvent in (b) is pentane, and the solvent in (d) is benzene.

8. A process according to claim 5 wherein the cyclohexylbenzene separated in (a) is recycled to oxidation, the cyclohexylbenzene separated from paraffin solvent in (b) is recycled to oxidation, the alcohol separated in (c) is recycled to step (a), and the water separated in (d) is recycled to step (a).

* * * * *